(12) United States Patent
Yamashita

(10) Patent No.: US 6,759,568 B2
(45) Date of Patent: Jul. 6, 2004

(54) HIGH ESTROGEN-SENSITIVE MEDAKA FISH

(75) Inventor: Ichiro Yamashita, Higashihiroshima (JP)

(73) Assignee: President of Hiroshima University, Higashihiroshima (JP)

( * ) Notice: Subject to any disclaimer, the term of this patent is extended or adjusted under 35 U.S.C. 154(b) by 0 days.

(21) Appl. No.: 09/893,666

(22) Filed: Jun. 29, 2001

(65) Prior Publication Data

US 2002/0129386 A1 Sep. 12, 2002

(30) Foreign Application Priority Data

Aug. 17, 2000 (JP) ........................................ 2000-247729

(51) Int. Cl.$^7$ ........................ G01N 33/00; A01K 67/00; A01K 67/027

(52) U.S. Cl. .................................. 800/20; 800/8; 800/3

(58) Field of Search ............................... 800/3, 13, 20, 800/21, 25

(56) References Cited

U.S. PATENT DOCUMENTS 5,903,305 A    5/1999    Yamamoto

FOREIGN PATENT DOCUMENTS

| EP | 1 180 684 A1 * | 2/2002 | .......... G01N/33/18 |
|----|----------------|--------|----------------------|
| JP | 2000-201688    | 7/2000 | |
| WO | WO 00/49150    | 8/2000 | |

OTHER PUBLICATIONS

Patent Abstracts of Japan, JP 2001 122899, May 8, 2001.
T. Kawahara, et al., Zoological Science, vol. 17, No. 5, pp. 643–649, "Cloning and Expression of Genomic and Complementary DNAs Encoding and Estrogen Receptor in the Medaka Fish, *Oryzias Latipes*", Jul. 2000.
H. Okada, et al., Database Swall EBI, AN D28954, "Oryzias SP. mRNA for Estrogen Receptor, Complete CDS", Apr. 23, 1994 and H. Okada, et al., Database Swall EBI, AN P50241, "*Oryzia Latipes* Estrogen Receptor", Oct. 1, 1996.
S. Tagaki, et al., Molecular Marine Biology and Biotechnology, vol. 3, No. 4, pp. 192–199, "An Efficient Expression Vector for Transgenic Medaka Construction", Aug. 1, 1994.
M. Gray, et al., Environmental Toxicology and Chemistry, vol. 18, No. 11, pp. 2587–2594, "Reproductive Success and Behavior of Japanese Medaka (*Oryzias Latipes*) Exposed to 4–Tert–Octylphenol", Nov. 1999.

* cited by examiner

Primary Examiner—Deborah J. Reynolds
Assistant Examiner—Joseph Woitach
(74) Attorney, Agent, or Firm—Oblon, Spivak, McClelland, Maier & Neustadt, P.C.

(57) ABSTRACT

(1) Transgenic medaka fish into which a polynucleotide having the nucleotide sequence from 211 to 1935 position represented by Sequence ID No: 1 is introduced, (2) A method of producing medaka fish having one or more thrombi, comprising the step of raising the transgenic medaka fish described in (1) in the presence of estrogen, (3) Medaka fish having one or more thrombi produced by the method described in (2), and (4) A method of testing an estrogen-like acting substance, comprising the steps of raising the transgenic medaka fish described in (1) in test water, and observing whether or not one or more thrombi are formed in the medaka fish after the raising step.

28 Claims, No Drawings

SEQUENCE LISTING

<160> NUMBER OF SEQ ID NOS: 7

<210> SEQ ID NO 1
<211> LENGTH: 2764
<212> TYPE: DNA

<213> ORGANISM: Oryzias latipes
<220> FEATURE:
<221> NAME/KEY: CDS
<222> LOCATION: (211)..(1935)
<223> OTHER INFORMATION:

<400> SEQUENCE: 1

```
gtctcgctgc tagatgcctg tcaggcaggc agagaggaag cagcccgtgt tgcgcagcac      60
atctgaggat gattcatgag taagagacag agctcggtgc agatcaggca gctgttcgga     120
ccagcactca gatccaggat cagcccagcc tcctcagagc tggagaccct ctccccacct     180
cgcctctcgc cccgtgaccc cctcggtgac atg tac cct gaa gag agc cgg ggt     234
                                  Met Tyr Pro Glu Glu Ser Arg Gly
                                    1               5 tct gga ggg gtg gct gct gtg gac ttt ttg gaa ggg acg tac gac tat     282
Ser Gly Gly Val Ala Ala Val Asp Phe Leu Glu Gly Thr Tyr Asp Tyr
         10                  15                  20 gcc gcc ccc aac cct gcc acg act ccc ctt tac agc cag tcc agc acc     330
Ala Ala Pro Asn Pro Ala Thr Thr Pro Leu Tyr Ser Gln Ser Ser Thr
 25                  30                  35                  40 ggc tac tac tct gct ccc ctg gaa aca aac gga ccc ccc tca gaa ggc     378
Gly Tyr Tyr Ser Ala Pro Leu Glu Thr Asn Gly Pro Pro Ser Glu Gly
             45                  50                  55 agt ctg cag tcc ctg ggc agt ggg ccg acg agc cct ctg gtt ttt gtg     426
Ser Leu Gln Ser Leu Gly Ser Gly Pro Thr Ser Pro Leu Val Phe Val
         60                  65                  70 ccc tcc agc ccc aga ctc agt ccc ttt atg cat cca ccc agc cac cac     474
Pro Ser Ser Pro Arg Leu Ser Pro Phe Met His Pro Pro Ser His His
 75                  80                  85 tat ctg gaa acc act tcc acg ccc gtt tac aga tcc agc cac cag gga     522
Tyr Leu Glu Thr Thr Ser Thr Pro Val Tyr Arg Ser Ser His Gln Gly
             90                  95                 100 gcc tcc agg gag gac cag tgc ggc tcc cgg gag gac acg tgc agc ctg     570
Ala Ser Arg Glu Asp Gln Cys Gly Ser Arg Glu Asp Thr Cys Ser Leu
105                 110                 115                 120 ggg gag tta ggc gcc gga gcc ggg gct ggg ggg ttt gag atg gcc aaa     618
Gly Glu Leu Gly Ala Gly Ala Gly Ala Gly Gly Phe Glu Met Ala Lys
                125                 130                 135 gac acg cgt ttc tgc gcc gtg tgc agc gac tac gcc tct ggg tac cac     666
Asp Thr Arg Phe Cys Ala Val Cys Ser Asp Tyr Ala Ser Gly Tyr His
            140                 145                 150 tat ggg gtg tgg tct tgt gag ggc tgc aag gcc ttc ttc aag agg agc     714
Tyr Gly Val Trp Ser Cys Glu Gly Cys Lys Ala Phe Phe Lys Arg Ser
        155                 160                 165 atc cag ggt cac aat gac tat atg tgc cca gcg acc aat cag tgc act     762
Ile Gln Gly His Asn Asp Tyr Met Cys Pro Ala Thr Asn Gln Cys Thr
    170                 175                 180 att gac aga aat cgg agg aag agc tgc cag gct tgt cgt ctt agg aag     810
Ile Asp Arg Asn Arg Arg Lys Ser Cys Gln Ala Cys Arg Leu Arg Lys
185                 190                 195                 200 tgt tac gaa gtg gga atg atg aaa ggc ggt gtg cgc aag gac cgc att     858
Cys Tyr Glu Val Gly Met Met Lys Gly Gly Val Arg Lys Asp Arg Ile
                205                 210                 215 cgc att tta cgg cgt gac aaa cgg cgg aca ggc gtt ggt gat gga gac     906
Arg Ile Leu Arg Arg Asp Lys Arg Arg Thr Gly Val Gly Asp Gly Asp
            220                 225                 230 aag gtt gta aag ggt cag gag cat aaa acg gtg cat tat gat gga agg     954
Lys Val Val Lys Gly Gln Glu His Lys Thr Val His Tyr Asp Gly Arg
        235                 240                 245 aaa cgc agc agc aca gga gga gga gga gga gga gga gga aga ctg        1002
```

-continued

```

Lys Arg Ser Ser Thr Gly Gly Gly Gly Gly Gly Gly Arg Leu
250             255                 260 tct gtg acc agc ata cct cct gag cag gtg ctg ctc ctc ctt cag ggc        1050
Ser Val Thr Ser Ile Pro Pro Glu Gln Val Leu Leu Leu Leu Gln Gly
265                 270                 275                 280 gcc gag ccc ccg ata ctc tgc tcg cgt cag aag ttg agc cga ccg tac        1098
Ala Glu Pro Pro Ile Leu Cys Ser Arg Gln Lys Leu Ser Arg Pro Tyr
                285                 290                 295 acc gag gtc acc atg atg acc ctg ctc acc agc atg gca gac aag gag        1146
Thr Glu Val Thr Met Met Thr Leu Leu Thr Ser Met Ala Asp Lys Glu
300                 305                 310 ctg gtc cac atg atc gcc tgg gcc aag aag ctc cca ggt ttt ctg cag        1194
Leu Val His Met Ile Ala Trp Ala Lys Lys Leu Pro Gly Phe Leu Gln
            315                 320                 325 ctg tcc ctg cac gat cag gtg ctg ctg gag agc tcg tgg ctg gag            1242
Leu Ser Leu His Asp Gln Val Leu Leu Glu Ser Ser Trp Leu Glu
330                 335                 340 gtg ctc atg atc ggc ctc att tgg agg tcc atc cac tgt ccc ggg aag        1290
Val Leu Met Ile Gly Leu Ile Trp Arg Ser Ile His Cys Pro Gly Lys
345                 350                 355                 360 ctc atc ttt gca caa gac ctc atc ctg gac agg aat gag gga gac tgc        1338
Leu Ile Phe Ala Gln Asp Leu Ile Leu Asp Arg Asn Glu Gly Asp Cys
                365                 370                 375 gtg gaa ggc atg acg gag atc ttc gac atg ctg ctg gcc act gct tcc        1386
Val Glu Gly Met Thr Glu Ile Phe Asp Met Leu Leu Ala Thr Ala Ser
                380                 385                 390 cgc ttc cgt gtg ctc aaa ctc aaa cct gag gaa ttc gtc tgc ctc aaa        1434
Arg Phe Arg Val Leu Lys Leu Lys Pro Glu Glu Phe Val Cys Leu Lys
            395                 400                 405 gct att att tta ctc aac tcc ggt gct ttt tct ttc tgc acc ggc acc        1482
Ala Ile Ile Leu Leu Asn Ser Gly Ala Phe Ser Phe Cys Thr Gly Thr
410                 415                 420 atg gag cca ctt cac aac agc gcg gcg gtt cag agc atg ctg gac acc        1530
Met Glu Pro Leu His Asn Ser Ala Ala Val Gln Ser Met Leu Asp Thr
425                 430                 435                 440 atc aca gac gca ctc att cat tac atc agt cag tcg ggt tac ttg gcc        1578
Ile Thr Asp Ala Leu Ile His Tyr Ile Ser Gln Ser Gly Tyr Leu Ala
                445                 450                 455 cag gag cag gcg aga cgg cag gcc cag ctg ctc ctg ctg ctc tcc cac        1626
Gln Glu Gln Ala Arg Arg Gln Ala Gln Leu Leu Leu Leu Leu Ser His
                460                 465                 470 atc agg cac atg agc aac aaa ggc atg gag cac ctc tac agc atg aag        1674
Ile Arg His Met Ser Asn Lys Gly Met Glu His Leu Tyr Ser Met Lys
            475                 480                 485 tgc aag aac aaa gtc cct ctt tat gac ctc cta ctg gag atg ctc gat        1722
Cys Lys Asn Lys Val Pro Leu Tyr Asp Leu Leu Leu Glu Met Leu Asp
490                 495                 500 gcc cac cgc ctg cac cac ccc gtc aga gca ccc cag tcc ttg tcc caa        1770
Ala His Arg Leu His His Pro Val Arg Ala Pro Gln Ser Leu Ser Gln
505                 510                 515                 520 gtc gac aga gac cct ccc tcc acc agc agc ggc ggg ggt gga atc gct        1818
Val Asp Arg Asp Pro Pro Ser Thr Ser Ser Gly Gly Gly Gly Ile Ala
                525                 530                 535 ccc ggt tct ata tca gca tct cga ggc aga atc gag agt ccg agc aga        1866
Pro Gly Ser Ile Ser Ala Ser Arg Gly Arg Ile Glu Ser Pro Ser Arg
                540                 545                 550 ggc ccc ttt gct ccc agt gtc ctt cag tat gga ggg tcg cgt cct gac        1914
Gly Pro Phe Ala Pro Ser Val Leu Gln Tyr Gly Gly Ser Arg Pro Asp
            555                 560                 565
```

```
tgc acc ccg gcc ctt caa gac tgagcacaca gtccaaggcc cttttttgt        1965
Cys Thr Pro Ala Leu Gln Asp
    570                 575 ggctcaaggg ttcaggttgg gacaaggtga tgcttgattt aattttaaga attatttata  2025
aataagagtg gcgctgagag gagaagctcc cacaatgaac tgcctctgct tggtccagct  2085
tttgtgcagt cactttaatc tgcttatatt catctccttt gtaaacctga gcgtctcttt  2145
agcagctttt ttttgctctc caaacagcat gtggtagatt gtaaggttgc gtcccatgag  2205
ttctggtgat ttcaagaaaa tgagcagcta atgttttctg taaccgtctt gacccaagtg  2265
cacttcctct tggattaaag gggctaatgg gcattatttt gtctcttgta catatgggat  2325
ggctaagaat aatgagagta attgtcagat tttgtgtaga acttacccac aaatgcaatt  2385
ttaaaataag atttaaaaac aaaagaggca agatcaaacc tgagagcact gaagacacgc  2445
tgtagaaagc tgggtaaatt tgttatccac gtctatctct ggaaaggact ttgttctctg  2505
tgcctgcagc tcatttactc tgaacttgct acttgttgaa catttgtgca cttgtccgtg  2565
tttttctagc actgtagctt atgaacgctg agaaagaatc taatgctttg atgcacagat  2625
ttgccttgta ttgtacatct cagccacaaa cgtactttc gtccacaagt tgactgactg    2685
caccttgatt aaattgtcta aaagttcatt taaatgttga attctgtgaa aattaaaaag  2745
gcaattcctg tttctattt                                                2764

<210> SEQ ID NO 2
<211> LENGTH: 575
<212> TYPE: PRT
<213> ORGANISM: Oryzias latipes

<400> SEQUENCE: 2

Met Tyr Pro Glu Glu Ser Arg Gly Ser Gly Gly Val Ala Ala Val Asp
1               5                   10                  15

Phe Leu Glu Gly Thr Tyr Asp Tyr Ala Ala Pro Asn Pro Ala Thr Thr
                20                  25                  30

Pro Leu Tyr Ser Gln Ser Ser Thr Gly Tyr Tyr Ser Ala Pro Leu Glu
            35                  40                  45

Thr Asn Gly Pro Pro Ser Glu Gly Ser Leu Gln Ser Leu Gly Ser Gly
        50                  55                  60

Pro Thr Ser Pro Leu Val Phe Val Pro Ser Ser Pro Arg Leu Ser Pro
65                  70                  75                  80

Phe Met His Pro Pro Ser His His Tyr Leu Glu Thr Thr Ser Thr Pro
                85                  90                  95

Val Tyr Arg Ser Ser His Gln Gly Ala Ser Arg Glu Asp Gln Cys Gly
                100                 105                 110

Ser Arg Glu Asp Thr Cys Ser Leu Gly Glu Leu Gly Ala Gly Ala Gly
            115                 120                 125

Ala Gly Gly Phe Glu Met Ala Lys Asp Thr Arg Phe Cys Ala Val Cys
        130                 135                 140

Ser Asp Tyr Ala Ser Gly Tyr His Tyr Gly Val Trp Ser Cys Glu Gly
145                 150                 155                 160

Cys Lys Ala Phe Phe Lys Arg Ser Ile Gln Gly His Asn Asp Tyr Met
                165                 170                 175

Cys Pro Ala Thr Asn Gln Cys Thr Ile Asp Arg Asn Arg Arg Lys Ser
                180                 185                 190

Cys Gln Ala Cys Arg Leu Arg Lys Cys Tyr Glu Val Gly Met Met Lys
            195                 200                 205
```

-continued

Gly Gly Val Arg Lys Asp Arg Ile Arg Ile Leu Arg Arg Asp Lys Arg
         210                 215                 220

Arg Thr Gly Val Gly Asp Gly Asp Lys Val Val Lys Gly Gln Glu His
225                 230                 235                 240

Lys Thr Val His Tyr Asp Gly Arg Lys Arg Ser Ser Thr Gly Gly Gly
                245                 250                 255

Gly Gly Gly Gly Gly Gly Arg Leu Ser Val Thr Ser Ile Pro Pro Glu
            260                 265                 270

Gln Val Leu Leu Leu Gln Gly Ala Glu Pro Pro Ile Leu Cys Ser
                275                 280                 285

Arg Gln Lys Leu Ser Arg Pro Tyr Thr Glu Val Thr Met Met Thr Leu
    290                 295                 300

Leu Thr Ser Met Ala Asp Lys Glu Leu Val His Met Ile Ala Trp Ala
305                 310                 315                 320

Lys Lys Leu Pro Gly Phe Leu Gln Leu Ser Leu His Asp Gln Val Leu
                325                 330                 335

Leu Leu Glu Ser Ser Trp Leu Glu Val Leu Met Ile Gly Leu Ile Trp
            340                 345                 350

Arg Ser Ile His Cys Pro Gly Lys Leu Ile Phe Ala Gln Asp Leu Ile
        355                 360                 365

Leu Asp Arg Asn Glu Gly Asp Cys Val Glu Gly Met Thr Glu Ile Phe
    370                 375                 380

Asp Met Leu Leu Ala Thr Ala Ser Arg Phe Arg Val Leu Lys Leu Lys
385                 390                 395                 400

Pro Glu Glu Phe Val Cys Leu Lys Ala Ile Ile Leu Leu Asn Ser Gly
                405                 410                 415

Ala Phe Ser Phe Cys Thr Gly Thr Met Glu Pro Leu His Asn Ser Ala
            420                 425                 430

Ala Val Gln Ser Met Leu Asp Thr Ile Thr Asp Ala Leu Ile His Tyr
        435                 440                 445

Ile Ser Gln Ser Gly Tyr Leu Ala Gln Glu Gln Ala Arg Arg Gln Ala
    450                 455                 460

Gln Leu Leu Leu Leu Leu Ser His Ile Arg His Met Ser Asn Lys Gly
465                 470                 475                 480

Met Glu His Leu Tyr Ser Met Lys Cys Lys Asn Lys Val Pro Leu Tyr
                485                 490                 495

Asp Leu Leu Leu Glu Met Leu Asp Ala His Arg Leu His His Pro Val
            500                 505                 510

Arg Ala Pro Gln Ser Leu Ser Gln Val Asp Arg Asp Pro Pro Ser Thr
        515                 520                 525

Ser Ser Gly Gly Gly Gly Ile Ala Pro Gly Ser Ile Ser Ala Ser Arg
    530                 535                 540

Gly Arg Ile Glu Ser Pro Ser Arg Gly Pro Phe Ala Pro Ser Val Leu
545                 550                 555                 560

Gln Tyr Gly Gly Ser Arg Pro Asp Cys Thr Pro Ala Leu Gln Asp
                565                 570                 575

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 3

```
                                    -continued
tcggtgacat gtaccctgaa                                                    20

<210> SEQ ID NO 4
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
ctgtgtgctc agtcttgaag                                                    20

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
cttccgtgtg ctcaaactca                                                    20

<210> SEQ ID NO 6
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
gtaggaggtc ataaagaggg                                                    20

<210> SEQ ID NO 7
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
gagggacttt gttcttgcac                                                    20
```

HIGH ESTROGEN-SENSITIVE MEDAKA FISH

CROSS-REFERENCE TO RELATED APPLICATIONS

This application is based upon and claims the benefit of priority from the prior Japanese Patent Application No. 2000-247729, filed Aug. 17, 2000, the entire contents of which are incorporated herein by reference.

BACKGROUND OF THE INVENTION

1. Field of the Invention

The present invention relates to high estrogen-sensitive medaka fish, and more specifically, to transgenic medaka fish having a medaka-derived estrogen receptor gene introduced.

The transgenic medaka fish of the present invention can be used to detect an estrogen-like endocrine disrupting chemicals, and also used as an experimental animal for elucidating development mechanism of thrombosis and as bioassay system for developing a therapeutic agent of thrombosis.

2. Description of the Related Art

Recently, the effects of chemical substances present in the environment upon endocrine system of an organism have been intensively studied, and have attracted a high interest increasingly. Since many chemical substances having endocrine disrupting activity upon an organism exhibit estrogen-like action, most of studies are directed to estrogen which is a female hormone.

Pollution of rivers with such estrogen-like chemical substances has constituted a social problem on a global scale. To detect the estrogen-like chemical substances from a river in the present invention, we tried the use of medaka fish which has excellent features as an experimental animal. However, the medaka fish cannot be used as an aquatic animal for testing environmental water, since it is not sensitive even to an extremely small amount of estrogen. This problem was found for the first time by the present inventor in the course of making the present invention.

BRIEF SUMMARY OF THE INVENTION

The present invention was made to overcome the aforementioned problem. An object of the present invention is to provide transgenic medaka fish having sensitivity to a very small amount of estrogen. Another object of the present invention is to provide a method of producing medaka fish having one or more thrombi by using the transgenic medaka fish, and to provide the medaka fish having one or more thrombi produced by the method. A further object of the present invention is to provide a method of testing an estrogen-like acting substance by using the transgenic medaka fish.

To attain the aforementioned objects, the present inventor have succeeded in preparing transgenic medaka fish having a medaka-derived estrogen receptor gene introduced, namely, high estrogen-sensitive medaka fish.

The present invention was made based upon such achievement.

To be more specific, the present invention was achieved by the means described below.

(1) A polynucleotide having a nucleotide sequence represented by Sequence ID No: 1.

(2) A polynucleotide comprising the nucleotide sequence from 211 to 1935 position represented by Sequence ID No: 1.

(3) A protein having an amino acid sequence encoded by the polynucleotide described in (2).

(4) A recombinant vector containing the polynucleotide described in (1) or (2).

(5) Transgenic medaka fish into which the polynucleotide described in (1) or (2) is introduced.

(6) A method of producing medaka fish having one or more thrombi, comprising the step of raising the transgenic medaka fish described in (5) in the presence of estrogen.

(7) Medaka fish having one or more thrombi, which is obtained by raising the transgenic medaka fish described in (5) in the presence of estrogen.

(8) A method of testing an estrogen-like action in test water, comprising the steps of:
raising the transgenic medaka fish described in (5) in the test water; and
observing whether or not one or more thrombi are formed in the medaka fish after the raising step.

(9) The method described in (8), wherein the test water is water taken from environment.

(10) The method described in (8), wherein the test water is water having a test substance added.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

Now, the present invention will be explained in detail.

In the present invention, the medaka fish to be used in cloning an estrogen receptor gene and the medaka fish to be used in introducing the cloned gene are not particularly limited, as long as they belong to a species *Oryzias latipes*. The medaka fish actually used in the present invention were obtained from the BioScience Center, Nagoya University. The obtained medaka fish were grown while feeding Tetramin (Tetra) in an amount of about 1–10 mg/day.

It should be noted that fertilized eggs of the medaka fish cannot be deposited, because a technology for resuming the development of a freeze-stored egg, as the need arises, has not yet been established. Therefore, the medaka fish used in the present invention are now raised under control of the present inventor with responsibility. As described in the above, the medaka fish to be used in the present invention are not limited to those raised by the present inventor, and any medaka fish may be used in the present invention.

{Cloning of Medaka-Derived Estrogen Receptor Gene}

The medaka-derived estrogen receptor gene of the present invention is cloned from liver cDNA library of adult medaka fish. More specifically, the medaka-derived estrogen receptor cDNA is cloned by preparing a probe based on a nucleotide sequence of a human-derived estrogen receptor gene and screening the above cDNA library by use of the probe.

The nucleotide sequence of the cloned estrogen receptor cDNA is determined, and the amino acid sequence predicted from the nucleotide sequence is determined. The nucleotide sequence of the medaka-derived estrogen receptor cDNA and the amino acid sequence are shown by Sequence ID No: 1 and Sequence ID No: 2, respectively in the Sequence Listing.

In the present invention, the nucleotide sequence for expressing medaka estrogen receptor may have arbitrary length, as long as it comprises at least a coding region (i.e., the nucleotide sequence from 211 to 1935 position represented by Sequence ID No: 1). Furthermore, in the present invention, the amino acid sequence of the medaka estrogen receptor may also have deletion, addition and/or substitution of one or several amino acids in the amino acid sequence represented by Sequence ID No: 2, as long as it has the same function as the protein consisting of the amino acid sequence represented by Sequence ID No: 2.

{Preparation of Recombinant Vector}

The medaka-derived estrogen receptor cDNA cloned by the aforementioned method is introduced into a vector. The introduction of the cDNA into a vector can be performed in accordance with a known genetic engineering process. In this manner, it is possible to prepare a recombinant vector into which the medaka-derived estrogen receptor gene is inserted.

The vector to be used in the present invention is not particularly limited, as long as it can express the protein encoded by a foreign gene inserted therein. In the present invention, it is preferable to use a plasmid having a promoter sequence and a poly (A) signal sequence, as a vector. For example, as described later in examples, a new plasmid vector is constructed by purifying each DNA fragment from another plasmid containing a DNA fragment of a medaka actin promoter and from another plasmid containing a DNA fragment of a SV40 poly (A) signal, and the resultant plasmid vector may be used.

{Preparation of Transgenic Medaka Fish}

The recombinant vector prepared as mentioned above is transferred into a nucleus of a medaka fertilized egg, thereby preparing transgenic medaka fish capable of expressing the estrogen receptor gene in an excessive amount. As the medaka fertilized egg to be transformed in the present invention, an embryo at a single-cell stage or a two-cell stage within one hour after fertilization is preferable. The recombinant vector can be transferred into the fertilized egg by means of a known microinjection procedure.

The fertilized eggs which have been subjected to the gene transfer operation are preferably hatched in a medaka physiological saline solution (7.5 g/L NaCl, 0.2 g/L KCL, 0.2 g/L $CaCl_2$, 0.02 g/L $NaHCO_3$) at 25–28° C. The hatched medaka fish are raised for about 4 months until they become adult fish.

From the adult fish, the fish actually having the gene introduced are screened by the following method. A DNA is first extracted from the adult fish. Then, from the extracted DNA, the estrogen receptor gene is amplified by a PCR, and the amplified DNA fragment is subjected to electrophoresis. The estrogen receptor gene inherently present in the chromosome of wild medaka fish has intron, whereas the estrogen receptor gene introduced into the medaka fish herein is a cDNA having no intron. Therefore, two types of estrogen receptor genes can be distinguished by electrophoresis on the basis of the difference of the size of DNA bands. By such procedure, it is possible to screen the medaka fish having the gene successfully introduced. However, it is not clear whether or not the estrogen receptor gene is introduced into the chromosome of a germ cell (sperm or egg) of the medaka fish screened in this step.

Subsequently, the medaka fish having the estrogen receptor gene introduced into the chromosome of a germ cell are screened by the following method. The medaka fish which has been confirmed to have the gene introduced by the aforementioned method is crossed with wild medaka fish, thereby obtaining offspring. If the medaka fish inheriting the estrogen receptor gene introduced is identified among the offspring, its parent turns out to be desired medaka fish having the estrogen receptor gene introduced in the chromosome of a germ cell. Whether or not the medaka offspring inherits the introduced gene can be identified, in the same way, by electrophoresis on the basis of the difference of the size of DNA bands between the introduced gene and the inherent gene.

The screened medaka fish having the estrogen receptor gene introduced in the chromosome can inherit the gene from generation to generation. Such medaka fish corresponds to a desired transgenic medaka fish of the present invention.

The expression of the estrogen receptor gene in the transgenic medaka fish of the present invention was checked by RT-PCR, and it was confirmed that the estrogen receptor gene was actually expressed. On the other hand, the expression of the estrogen receptor gene was rarely detected in wild medaka fish. As described above, the transgenic medaka fish of the present invention has a large number of estrogen receptors by the expression of the introduced gene. For this reason, the transgenic medaka fish of the present invention shows sensitivity even to a very small amount of estrogen.

{Preparation of Medaka Fish Having One or More Thrombi}

In the present invention, it was found that the medaka fish having one or more thrombi can be prepared, even if the transgenic medaka fish of the present invention is raised in the presence of estrogen whose concentration is lower than that capable of inducing the formation of a thrombus in wild medaka fish.

As the transgenic medaka fish to be used for the formation of a thrombus, it is preferable to employ an embryo within 12–24 hours after fertilization, because the formation of a thrombus in the embryo can be easily observed under a dissecting microscope. To form a thrombus in the transgenic medaka fish of the present invention, it is sufficient to contain estrogen in the concentration of 10–20 ng/L, preferably 100–200 ng/L, in the environment for raising medaka fish. It is noted that wild medaka fish require estrogen in the concentration of 4 mg/L or more in order to form a thrombus. As the term of raising the medaka fish in the presence of estrogen, a period of three to four days is necessary for the formation of a thrombus. The growth conditions may be the same as those generally employed for raising medaka fish.

It is possible to confirm the formation of a thrombus under a dissecting microscope.

The medaka fish having one or more thrombi prepared in this manner is useful for studying therapy of thrombosis.

{Method of Testing an Estrogen-Like Acting Substance}

The presence or absence of the estrogen-like acting substance can be detected by growing the transgenic medaka fish of the present invention in test water to be checked for the estrogen-like action and then observing whether or not a thrombus is formed in the medaka fish.

As the transgenic medaka fish to be used in order to detect an estrogen-like acting substance, an embryo within 12–24 hours after fertilization is preferable because it is easily observed under a dissecting microscope.

The "test water" used herein may be either water collected from the environment (river etc.), which may perhaps contain an estrogen-like acting substance, or water added a chemical substance, which may perhaps act like estrogen, as a test substance. When the former water taken from the environment is used, it is possible to detect the presence or absence of the estrogen-like acting substance in the environmental water. When the latter water added a test substance is used, the estrogen-like action of the test substance can be checked.

When the test substance is added to the test water, it is preferable to set a concentration thereof at 10 ng/L to 1 mg/L. As the period for raising the medaka fish in the test water, 3–6 days are appropriate. The growth conditions may be the same as those usually raising medaka fish.

It is possible to observe the formation of a thrombus under a dissecting microscope.

In fact, an estrogen-like acting chemical substance is known to have an endocrine disrupting action even in an extremely small amount. Therefore, the transgenic high estrogen-sensitive medaka fish of the present invention is very useful in both the aforementioned tests of the environmental water and the test substance.

EXAMPLES

Now, examples of the present invention will be explained.

Cloning of Medaka-derived Estrogen Receptor cDNA

1. Construction of Liver cDNA Library of Medaka

Total RNA (10 mg) was obtained from 20 livers of female adult medaka fish by use of RNeasy Maxi Kit (QIAGEN #75162) in accordance with the attached protocol. Then, mRNA (100 µg) was isolated from the obtained total RNA by using Oligotex TM-dT30<Super> (TaKaRa w9021B) in accordance with the attached protocol. Using the isolated mRNA, cDNA (about 10 µg) was synthesized by a cDNA Synthesis Kit (STRATAGENE SC200401) in accordance with the attached protocol. The synthesized cDNA (1 µg) was ligated with λZAPII (STRATAGENE SC237211) (1 µg) by using Ligation High (STRATAGENE LGK-101) in accordance with the attached protocol. The total amount of the reaction solution is packaged by using Gigapack III Packaging Extracts (STRATAGENE SC200202) in accordance with the attached protocol. In this manner, a cDNA library constituted of about one million phages was prepared.

2. Screening

Plasmid pOR8 (about 1 µg) having a human-derived estrogen receptor cDNA (Nature, Vol. 320, pages 134–139, 1986) was digested with a restriction enzyme EcoRI, and then the total amount containing the digested fragments was subjected to electrophoresis on 1.0% agarose gel. After the gel was stained with ethidium bromide, a piece of the gel containing an estrogen receptor cDNA fragment (about 2.1 kb) was excised out, while the size of the DNA fragment was checked on a UV transilluminator. From the gel piece, the estrogen receptor cDNA fragment was purified by using Ultrafree-MC (Millipore) in accordance with the attached protocol. Using the purified cDNA fragment as a probe, the aforementioned cDNA library was screened by the method described in "Molecular cloning—a laboratory manual" (Second edition, J. Sambrook, E. F. Fritsch, T. Maniatis, Cold Spring Harbor Laboratory Press, Pages 2,108–2,125, 1989). In this manner, a recombinant phage having a Medaka estrogen receptor cDNA was isolated. From the isolated phage, plasmid pMER having the Medaka estrogen receptor cDNA was obtained by using an ExAssist™ helper phage (STRATAGENE SC237211) in accordance with the attached protocol.

3. Determination of Nucleotide Sequence

The nucleotide sequence was analyzed by a Dye Terminator Cycle Sequencing method using an Applied Biosystems 373A DNA Autosequencer. As a result of the nucleotide sequence analysis, it was found that the obtained cDNA encodes a protein consisting of 620 amino acids, and that the amino acid sequence of the protein has a high homology with those of estrogen receptors of human and other vertebrates. Therefore, it is conceivable that the cDNA encodes Medaka estrogen receptor.

Preparation of Plasmid pOL22 to be Injected in Medaka Fertilized Eggs

To express the above isolated Medaka estrogen receptor cDNA in a cell of medaka fish, a promoter derived from a medaka β-actin gene was ligated to the upstream of the 5' end of the cDNA, and an SV40 virus-derived poly (A) addition signal was ligated to the downstream of the 3' end of the cDNA. Plasmid pOL22 having such chimera gene was prepared by the following method.

1. Plasmid pOBA-109 (about 1 µg) (Molecular Marine Biology and Biotechnology, Vol. 3, pages 192–199, 1994) having a medaka β-actin promoter was digested with two types of restriction enzymes of SphI (TOYOBO) and PstI (TOYOBO) in accordance with the attached protocol. After the reaction solution was treated at 70° C. for 10 minutes, the total amount of the solution was further treated with Klenow polymerase (TOYOBO) (2 µL) in accordance with the attached protocol. Thereafter, the reaction solution was treated at 70° C. for 10 minutes, and then the total amount of the solution was subjected to electrophoresis on 1.0% agarose gel. As a result, a gel piece containing about 3.5 kb of a medaka β-actin promoter DNA fragment was excised out. From the excised gel piece, the medaka β-actin promoter DNA fragment was purified by using Ultrafree-MC (Millipore) in accordance with the attached protocol.

2. Plasmid pS65T-Cl (about 1 µg) (Clontech) having the SV40 poly (A) signal was digested with two types of restriction enzymes of AseI (TOYOBO) and NheI (TOYOBO) in accordance with the attached protocol. After the reaction solution was treated at 70° C. for 10 minutes, the total amount of the solution was further treated with Klenow polymerase (TOYOBO) (2 µL) in accordance with the attached protocol. Thereafter, the reaction solution was treated at 70° C. for 10 minutes, Bacterial alkaline phosphatase (TOYOBO) (2 µL) was added thereto, and the resultant solution was mixed and reacted at 60° C. for 2 hours. The total amount of the reaction solution was subjected to electrophoresis on 1.0% agarose gel, and a gel piece containing about 4.1 kb of the SV40 poly (A) signal DNA fragment was excised out. From the gel piece, the SV40 poly (A) signal DNA fragment was purified by using Ultrafree-MC (Millipore) in accordance with the attached protocol.

3. Two DNA fragments purified in the above (5 µL for each) each containing 0.1 µg of DNA were mixed with 10 µL of solution I (TaKaRa) of DNA Ligation System Ver. 2, and the mixture was incubated at 16° C. for about 12 hours. In this manner, the two DNA fragments were ligated to each other. Using the resultant reaction solution (10 µL), *E. coli* DH5α (TaKaRa, #9057) was transformed. From the obtained transformants, a plasmid was isolated by using NucleoBond Plasmid Kit (Clontech #K3001-1). The isolated plasmid was designated as pOL21.

4. Plasmid pOL21 (about 1 µg) was digested with a restriction enzyme SalI (TOYOBO) in accordance with the attached protocol. After the reaction solution was treated at 70° C. for 10 minutes, the total amount of the solution was further treated with Klenow polymerase (TOYOBO) (2 µL) in accordance with the attached protocol. Thereafter, the reaction solution was treated at 70° C. for 10 minutes, Bacterial alkaline phosphatase (TOYOBO) (2 µL) was added thereto, and the resultant solution was mixed and reacted at 60° C. for 2 hours. The total amount of the reaction solution was subjected to electrophoresis on 1.0% agarose gel, and a gel piece containing about 7.1 kb of a DNA fragment was excised out. From the gel piece, the DNA fragment was purified by using Ultrafree-MC (Millipore) in accordance with the attached protocol.

5. To amplify the medaka estrogen receptor cDNA, a reaction solution (50 µL) for PCR was prepared, in accordance with the attached protocol, by using plasmid pMER (10 ng) as a template; 25 pmole of Primer 1 (5'TCGGTGACATGTACCCTGAA-3') (Sequence ID No: 3) and 25 pmole of Primer 2 (5'-CTGTGTGCTCAGTCTTGAAG-3') (Sequence ID No: 4); and KOD polymerase (TOYOBQ) (1 µL). PCR was performed by repeating 25 cycles of the following program: 98° C. for 15 seconds, 65 C for 2 seconds, and 74° C. for 30 seconds. After the reaction, the reaction solution containing the PCR product was stored at 4° C. An aliquot (5 µL) of the reaction solution containing the PCR product was subjected to electrophoresis on 1% agarose gel. As a result, it was confirmed that the molecular size of the PCR product is about the same as that of a desired product (1.8 kb). From the remaining reaction solution, the amplified DNA fragment was purified by using SUPRECTM™-02(TaKaRa) in accordance with the attached protocol. The total amount of the purified DNA fragment was phosphated with 2 µL of T4 kinase (TOYOBQ) in accordance with the attached protocol. After the reaction, the resultant solution was treated at 70° C. for 10 minutes.

The DNA fragments (0.1 µg for each) finally obtained in the above steps 4 and 5 were ligated by using DNA Ligation System Ver.2 (TaKaRa) in accordance with the attached protocol. Using the resultant reaction solution (10 µL), *E. coli* DH5α (TaKaRa #9057) was transformed. From the obtained transformants, a plasmid was isolated by using NucleoBond Plasmid Kit (Clontech #K3001-1). The isolated plasmid was designated as pOL22.

Method of Preparing Transgenic Medaka Fish

1. About 500 of the medaka-fertilized eggs either at a single-cell stage or a two-cell stage were taken within one hour after fertilization, and stored at 6° C. until DNA injection. About 100 pL of DNA solution (containing 10 µg of plasmid pOL 22 per 1 mL) was injected into the cytoplasm of the fertilized egg by using a glass tube with a sharp end under a dissecting microscope. Thereafter, the fertilized eggs were divided into groups each consisting of 50 eggs. 50 eggs of each group were incubated at 25° C. in 40 mL of medaka physiological saline solution (containing 7.5 g of NaCl, 0.2 g of KCl, 0.2 g of $CaCl_2$, and 0.02 g of $NaHCO_3$ per liter) until they were hatched. As a result, about half of eggs were hatched. The hatched eggs were transferred to a water tank, and raised by feeding with Tetramin (Tetra) for about 4 months until they became adult fish. More specifically, the amount of Tetramin per day was set so as not to leave, and it was fed by dividing into three times in a day. As a result, about 50 medaka fish survived until they became adult fish.

Half of each caudal fin from the survived adult fish was cut off with scissors. DNA (20 µL) was extracted separately from each of the cut caudal fins by using a DNA extraction kit ISOHAIR (WAKO) in accordance with the attached protocol. A reaction solution (100 µL) for PCR was prepared, in accordance with the attached protocol, by using the extracted DNA (1 µL); two types of primers F1 (5'CTTCCGTGTGCTCAAACTCA-3' (Sequence ID No: 5) and R1 (5'GTAGGAGGTCATAAAGAGGG-3' (Sequence ID No: 6) (50 pmole for each); and Ex Taq (TaKaRa Ex Taq RR001B) (1 µL). After initial denaturing at 94° C. for 2 minutes, PCR was performed by repeating 30 cycles of the following program: 94° for 30 seconds, 60° C. for 30 seconds, and 72° C. for 90 seconds. Finally, the resultant solution was reacted at 72° C. for 6 minutes, and then it was stored at 4° C. An aliquot (10 µL) of the PCR solution containing the PCR product was subjected to electrophoresis on to agarose gel. In the case of medaka fish having no chimera gene injected, about 1 kb of DNA band was detected, which was derived from amplification of estrogen receptor gene inherently present in the chromosome of wild medaka fish. In contrast, in the case of medaka fish having a chimera gene injected, a 320 by of DNA band derived from the chimera gene was detected in addition to the above about 1 kb of band. As a result, eight medaka fish with the chimera gene were obtained.

3. Eight medaka fish with the chimera gene were individually crossed with wild medaka fish. From each parent medaka fish, one hundred offspring were raised until they became adult fish. DNA (20 µL) was extracted from each caudal fin of these offspring by use of a DNA extraction kit ISOHAIR (WAKO) in accordance with the attached protocol. A reaction solution (100 µL) for PCR was prepared, in accordance with the attached protocol, by using the extracted DNA (1 µL); two types of primers (5'-CTTCCGTGTGCTCAAACTCA3') (Sequence ID No: 5) and (5'-GTAGGAGGTCATAAAGAGGG3') (Sequence ID No: 6) (50 pmole for each); and Ex Taq (TaKaRa Ex Tag RR001B) (1 µL). After initial denaturing at 94° C. for 2 minutes, PCR was performed by repeating 30 cycles of the following program: 94° C. for 30 seconds, 60° C. for 30 seconds, and 72° C. for 90 seconds. Finally, the resultant solution was reacted at 72° C. for 6 minutes, and then it was stored at 4° C. An aliquot (10 µL) of the PCR solution containing the PCR product was subjected to electrophoresis on 1% agarose gel. The offspring medaka fish having a 320 by of DNA band derived from the chimera gene was identified as transgenic medaka fish. As a result, only two of original eight medaka fish actually transferred the chimera gene into their offspring. Therefore, two strains of transgenic medaka fish (designated as strains A and C) were obtained. The number of the transgenic medaka fish obtained herein was small. However, these transgenic medaka fish were crossed with wild medaka fish, and thereby more than about 100 transgenic medaka fish have been maintained for each strain. In both strains of the transgenic medaka fish, about half of offspring obtained by crossing with wild medaka fish have the chimera gene. From this, it was found that either one of two homologous chromosomes had the chimera gene.

Expression of Chimera Gene in Transgenic Medaka Fish

The fact that the strains A and C of the transgenic medaka fish produce a mRNA encoding estrogen receptor in a larger amount than wild medaka fish, was demonstrated by the following method. RNA (30 µL) was extracted from about 30 fertilized eggs which were obtained by crossing the transgenic medaka with wild medaka fish and about 30 fertilized eggs which were obtained by mutual mating between wild medaka fish, by use of an RNeasy Mini Kit (QIAGEN) in accordance with the attached protocol. Then, a reaction solution (50 μL) for RT-PCR was prepared by using the extracted RNA (1 μL); three types of primers (50 pmole for each): F1 (Sequence ID No: 5), R1 (Sequence ID No: 6) mentioned above, and R2 (5'-GAGGGACTTTGTTCTTGCAC-3') (Sequence ID No: 7); and Ready-To-Go RT-PCR Beads (Amersham Pharmacia Biotech #27-9267-01) in accordance with the attached protocol. Alter performing initial reactions at 42° C. for 30 minutes and 959C for 5 minutes, RT-PCR was performed by repeating the 30 cycles of the following program: 950C for 30 seconds, 60° C. for 30 seconds, and 72° C. for 90 seconds. After completion of the reaction, the reaction solution was stored at 4° C. An aliquot (10 μL) of the RT-PCR solution was subjected to electrophoresis on 1% agarose gel. Thereafter, DNA on the gel was transferred onto a membrane in accordance with the method described in "Molecular cloning—a laboratory manual" (Second edition, J. Sambrook, E. F. Fritsch, T. Maniatis, Cold Spring Harbor Laboratory Press, Pages 9.31–9.62, 1989). Then, Southern Hybridization was performed by using an EcoRI-SaU fragment (354 bp) of the estrogen receptor cDNA as a probe. A clear band of about 300 by was detected in the fertilized eggs derived from the strains A and C of the transgenic medaka fish. Since the band from the strain C was nearly twice as dense as that from the strain A, it is conceivable that the strain C of the transgenic medaka fish produce the mRNA encoding estrogen receptor in an larger amount than the strain A of the transgenic medaka fish. However, no band was detected in the fertilized eggs derived from the wild medaka fish. From this fact, it is conceivable that the expression amount of the estrogen receptor niRNA is significantly low in the fertilized eggs from the wild medaka fish.

Formation of Thrombus by Estrogen in Transgenic Medaka Fish

Medaka physiological saline solutions (40 mL for each) containing 17 β-estradiol in an amount of 2 ng/L, 20 ng/L, 200 ng/L, 2 μg/L, 1 mg/L, and 4 mg/L were supplied in culture plates, respectively. Three sets were prepared for each concentration. About 30 fertilized eggs (W) of 12-hours after fertilization which were obtained by mutual mating between wild medaka fish, were placed in the first set of culture plates. About 30 fertilized eggs (A) of 12-hours after fertilization which were obtained by crossing the strain A of the transgenic medaka fish with wild medaka fish, were placed in the second set of culture plates. About 30 fertilized eggs (C) of 12-hours after fertilization which were obtained by crossing the strain C of the transgenic medaka fish with wild medaka fish, were placed in the third set of culture plates. After the culture plates were incubated at 25° C. for 3 days, medaka embryos were checked under dissecting microscope with respect to formation of a thrombus.

In almost 100% of the fertilized eggs (W), one or more thrombi were formed at the concentration of 4 mg/L of 17β-estradiol, but were not observed at the concentration of less than 4 mg/L. 1%, 3%, 8%, 49%, 55%, and 100% of the fertilized eggs (A) caused the formation of the thrombi at the concentrations of 2 ng/L, 20 ng/L, 200 ng/L, 2 μg/L, 1 mg/L, and 4 mg/L of 17β-estradiol, respectively. 19%, 41%, 75%, 73%, 60%, and 100% of the fertilized eggs (C) caused the formation of the thrombi at the same concentrations as mentioned above, respectively. It was therefore demonstrated that the estrogen sensitivities of fertilized eggs (A) and (C) are thousand times and hundred thousand times as high as that of the wild medaka fish, respectively.

{Effect of the Present Invention}

As described in the foregoing, the transgenic medaka fish of the present invention is high sensitive to an extremely low amount of estrogen, compared to non-transgenic medaka fish (i.e., wild medaka fish). Therefore, the transgenic medaka fish of the present invention is very useful as a novel aquatic animal whereby a very small amount of estrogen-like acting substance present in the environment can be detected quickly, easily, continuously, and inexpensively. By use of such a novel aquatic animal, it is possible to detect water pollution of rivers with an estrogen-like acting substance which is a social problem.

Also, if the fertilized eggs of the transgenic medaka fish of the present invention are raised in estrogen-containing water, it is possible to observe the formation of thrombus in a blood vessel. Therefore, the transgenic medaka fish of the present invention is useful as an experimental animal for elucidating the development mechanism of thrombosis caused by intake of estrogen due to the use of oral contraceptive and hormonotherapy in human. The animals conventionally used in thrombosis studies are rats and rabbits. However, they are expensive as experimental animal. In addition, the formation of a thrombus must be checked by injecting an angiographic agent followed by using a specific device. In contrast, the medaka fish used in the present invention has advantages of inexpensiveness and easiness. More specifically, since its fertilized egg is transparent, the thrombus can be observed easily and continuously under a dissecting microscope. Moreover, it is easy to prepare a sample for its biochemical analysis.

Furthermore, the transgenic medaka fish of the present invention can be used as a model animal for bioassay system of thrombosis, when a therapeutic agent of thrombosis is developed. Although the therapeutic agent of thrombosis has been developed based on administration by injection up to now, the use of the medaka fish of the present invention makes it possible to screen an oral therapeutic agent of thrombosis on a large scale.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A transgenic medaka fish comprising a polynucleotide having a nucleotide sequence of SEQ ID No: 1 encoding a medaka estrogen receptor, wherein said polynucleotide is operably linked to a promoter sequence that is capable of expressing sufficient amounts of the medaka estrogen receptor encoded by said polynucleotide, and wherein said transgenic medaka fish produces increased level of the estrogen receptor as compared to normal wild-type medaka fish and produces observable thrombi when cultured in the presence of estrogen.

2. A method of producing transgenic medaka fish having one or more thrombi, comprising raising the transgenic medaka fish of claim 1 in the presence of estrogen.

3. A transgenic medaka fish having one or more thrombi, which is obtained by raising the transgenic medaka fish of claim 1 in the presence of estrogen.

4. A method of testing an estrogen-like activity in test water, comprising:
   raising the transgenic medaka fish of claim 1 in test water; and
   observing whether or not one or more thrombi are formed in the medaka fish after said raising.

5. The method according to claim 4, wherein the test water is water taken from the environment.

6. The method according to claim 4, wherein the test water is water having a test substance added.

7. The transgenic medaka fish according to claim 1, wherein said promoter is the medaka beta-actin promoter.

8. A transgenic medaka fish comprising a polynucleotide having a nucleotide sequence corresponding to nucleotides 211 to 1935 of SEQ ID No: 1 encoding a medaka estrogen receptor, wherein said polynucleotide is operably linked to a promoter sequence that is capable of expressing sufficient amounts of the medaka estrogen receptor encoded by said polynucleotide, and wherein said transgenic medaka fish produces increased level of the estrogen receptor as compared to normal wild-type medaka fish and produces observable thrombi when cultured in the presence of estrogen.

9. A method of producing transgenic medaka fish having one or more thrombi, comprising raising the transgenic medaka fish of claim 8 in the presence of estrogen.

10. A transgenic medaka fish having of one or thrombi, which is obtained by raising the transgenic medaka fish of claim 8 in the presence of estrogen.

11. A method of testing an estrogen-like activity in test water, comprising:

raising the transgenic medaka fish of claim 8 in test water; and observing whether or not one or more thrombi are formed in the medaka fish after said raising.

12. The method according to claim 11, wherein the test water is water taken from the environment.

13. The method according to claim 11, wherein the test water is water having a test substance added.

14. The transgenic medaka fish according to claim 8, wherein said promoter is the medaka beta-actin promoter.

15. A transgenic medaka fish comprising a polynucleotide having a nucleotide sequence corresponding to nucleotides 211 to 1935 of SEQ ID No: 1 encoding a medaka estrogen receptor, wherein one or more nucleotides are added, deleted, or mutated and the protein encoded thereby has estrogen receptor activity, and wherein said polynucleotide is operably linked to a promoter sequence, that is capable of expressing sufficient amounts of the medaka estrogen receptor encoded by said polynucleotide, and wherein said transgenic medaka fish produces increased level of the estrogen receptor as compared to normal wild-type medaka fish and produces observable thrombi when cultured in the presence of estrogen.

16. A method of producing transgenic fish having one or more thrombi, comprising raising the transgenic medaka fish of claim 15 in the presence of estrogen.

17. A transgenic medaka fish having one or more thrombi, which is obtained by raising the transgenic medaka fish of claim 15 in the presence of estrogen.

18. A method of testing an estrogen-like activity in test water, comprising:

raising the transgenic medaka fish of claim 15 in test water; and observing whether or not one or more thrombi are formed in the medaka fish after said raising.

19. The method according to claim 18, wherein the test water is water taken from the environment.

20. The method according to claim 18, wherein the test water is water having a test substance added.

21. The transgenic medaka fish according to claim 15, wherein said promoter is the medaka beta-actin promoter.

22. A transgenic medaka fish comprising a polynucleotide encoding a medaka estrogen receptor having an amino acid sequence of SEQ ID No. 2, wherein said polynucleotide is operably linked to a promoter sequence that is capable of expressing sufficient amounts of the medaka estrogen receptor encoded by said polynucleotide, and wherein said transgenic medaka fish produces increased level of the estrogen receptor as compared to normal wild-type medaka fish and produces observable thrombi when cultured in the presence of estrogen.

23. A method of producing transgenic medaka fish having one or more thrombi, comprising raising the transgenic medaka fish of claim 22 in the presence of estrogen.

24. A transgenic medaka fish having one or more thrombi, which is obtained by raising the transgenic medaka fish of claim 22 in the presence of estrogen.

25. A method of testing an estrogen-like activity in test water, comprising:

raising the transgenic medaka fish of claim 22 in test water; and observing whether or not one or more thrombi are formed in the medaka fish after said raising.

26. The method according to claim 25, wherein the test water is water taken from the environment.

27. The method according to claim 25, wherein the test water is water having a test substance added.

28. The transgenic medaka fish according to claim 22, wherein said promoter is the medaka beta-actin promoter.

\* \* \* \* \*